(12) United States Patent
Wilson et al.

(10) Patent No.: US 9,247,730 B2
(45) Date of Patent: Feb. 2, 2016

(54) PESTICIDE COMPOSITIONS EXHIBITING ENHANCED ACTIVITY AND METHODS FOR PREPARING SAME

(71) Applicant: Dow AgroSciences, LLC, Indianapolis, IN (US)

(72) Inventors: Stephen L. Wilson, Zionsville, IN (US); Lei Liu, Carmel, IN (US); James D. Thomas, Fishers, IN (US); Raymond E. Boucher, Jr., Lebanon, IN (US); James E. Dripps, Carmel, IN (US); Margaret S. Kempe, Greenfieldd, IN (US); Martin C. Logan, Indianapolis, IN (US); Douglas J. Linscott, Pittsboro, IN (US); John M. Atkinson, Zionsville, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 111 days.

(21) Appl. No.: 14/309,568

(22) Filed: Jun. 19, 2014

(65) Prior Publication Data

US 2014/0303104 A1 Oct. 9, 2014
US 2015/0373971 A9 Dec. 31, 2015

Related U.S. Application Data

(62) Division of application No. 12/768,263, filed on Apr. 27, 2010, now Pat. No. 8,796,476.

(60) Provisional application No. 61/214,989, filed on Apr. 30, 2009, provisional application No. 61/277,974, filed on Oct. 1, 2009.

(51) Int. Cl.

| | |
|---|---|
| *A01N 25/08* | (2006.01) |
| *A01N 25/00* | (2006.01) |
| *A01N 43/22* | (2006.01) |
| *A01N 25/22* | (2006.01) |
| *A01N 35/06* | (2006.01) |
| *A01N 35/08* | (2006.01) |
| *A01N 37/36* | (2006.01) |
| *A01N 37/42* | (2006.01) |
| *A01N 43/00* | (2006.01) |
| *A01N 43/16* | (2006.01) |
| *A01N 43/90* | (2006.01) |
| *A01N 59/16* | (2006.01) |

(52) U.S. Cl.
CPC .............. *A01N 25/00* (2013.01); *A01N 25/08* (2013.01); *A01N 25/22* (2013.01); *A01N 35/06* (2013.01); *A01N 35/08* (2013.01); *A01N 37/36* (2013.01); *A01N 37/42* (2013.01); *A01N 43/00* (2013.01); *A01N 43/16* (2013.01); *A01N 43/22* (2013.01); *A01N 43/90* (2013.01); *A01N 59/16* (2013.01)

(58) Field of Classification Search
CPC ............................ A01N 43/22; A01N 25/00
USPC ............ 549/383, 275; 424/78.08, 78.31, 641, 424/646
See application file for complete search history.

(56) References Cited

U.S. PATENT DOCUMENTS

| | | | | |
|---|---|---|---|---|
| 2,168,064 | A | * | 8/1939 | Faloon ......................... 504/187 |
| 2,947,659 | A | * | 8/1960 | Rogers ......................... 424/631 |
| 3,886,125 | A | | 5/1975 | Chromecek |
| 3,929,453 | A | | 12/1975 | Dimitri et al. |
| 4,056,610 | A | | 11/1977 | Barber, Jr. et al. |
| 4,184,866 | A | | 1/1980 | Dellicolli et al. |
| 4,244,728 | A | | 1/1981 | Dellicolli et al. |
| 4,485,103 | A | | 11/1984 | Pasarela |
| 4,497,793 | A | | 2/1985 | Simkin |
| 4,557,755 | A | | 12/1985 | Takahashi et al. |
| 4,622,315 | A | | 11/1986 | Dureja et al. |
| 5,024,832 | A | | 6/1991 | Omata et al. |
| 5,190,764 | A | | 3/1993 | Chiba et al. |
| 5,202,242 | A | | 4/1993 | Mynderse et al. |
| 5,227,295 | A | | 7/1993 | Baker |
| 5,246,936 | A | | 9/1993 | Treacy et al. |

(Continued)

FOREIGN PATENT DOCUMENTS

| | | |
|---|---|---|
| CN | 101014247 | 8/2007 |
| DE | 10037670 | 2/2002 |

(Continued)

OTHER PUBLICATIONS

International Preliminary Report of Patentability; PCT/US2010/001246.

(Continued)

*Primary Examiner* — Sean Basquill
(74) *Attorney, Agent, or Firm* — Yung H. Lee; Carl D. Corvin; Maschoff Brennan

(57) ABSTRACT

Pest controlling compositions exhibiting enhanced pesticidal activity levels and methods for preparing the same are disclosed. In one embodiment, a method includes providing a liquid composition that includes at least one pesticide and at least one co-ingredient that enhances pesticidal activity of the composition compared to a composition dissimilar only in not having the at least one co-ingredient. The at least one co-ingredient may include at least one metal oxide, a combination of at least transition metal salt and at least one proteinaceous material or a combination of at least one proteinaceous material and at least one polymeric material. The method further includes spray drying the liquid composition to provide a solid composition. In one aspect of this embodiment, the solid composition provided by the spray drying exhibits enhanced pesticidal activity compared to the liquid composition.

9 Claims, No Drawings

(56) References Cited

U.S. PATENT DOCUMENTS

| | | | |
|---|---|---|---|
| 5,362,634 A | 11/1994 | Boeck et al. | |
| 5,436,355 A | 7/1995 | Demchak | |
| 5,529,772 A | 6/1996 | Lebo, Jr. | |
| 5,539,089 A | 7/1996 | Broughton et al. | |
| 5,571,901 A | 11/1996 | Boeck et al. | |
| 5,591,606 A | 1/1997 | Turner et al. | |
| 5,670,364 A | 9/1997 | Mynderse et al. | |
| 5,750,126 A | 5/1998 | Smith et al. | |
| 5,750,467 A | 5/1998 | Shasha et al. | |
| 5,939,089 A | 8/1999 | Wirtz et al. | |
| 6,001,981 A | 12/1999 | DeAmicis et al. | |
| 6,090,399 A | 7/2000 | Gosh et al. | |
| 6,143,526 A | 11/2000 | Baltz et al. | |
| 6,455,504 B1 | 9/2002 | Lewer et al. | |
| 6,585,990 B1 | 7/2003 | Huang | |
| 6,733,802 B1 | 5/2004 | Moorty et al. | |
| 6,919,464 B1 | 7/2005 | Crouse et al. | |
| 6,927,210 B1 | 8/2005 | Thompson et al. | |
| 6,955,818 B1 | 10/2005 | Hacket et al. | |
| 2003/0082236 A1 | 5/2003 | Mathiowitz et al. | |
| 2003/0108585 A1 | 6/2003 | Roe et al. | |
| 2003/0138500 A1 | 7/2003 | Parker et al. | |
| 2005/0112235 A1 | 5/2005 | Shefer et al. | |
| 2005/0203034 A1 | 9/2005 | Ahn et al. | |
| 2007/0020304 A1 | 1/2007 | Tamarkin et al. | |
| 2007/0104750 A1* | 5/2007 | Wilson et al. | 424/405 |
| 2007/0280981 A1 | 12/2007 | Birthisel | |
| 2008/0031832 A1 | 2/2008 | Wakefield et al. | |
| 2008/0108800 A1 | 5/2008 | Podhorez et al. | |
| 2011/0009350 A1* | 1/2011 | Pedersen et al. | 514/30 |

FOREIGN PATENT DOCUMENTS

| | | | |
|---|---|---|---|
| EP | 0111808 A2 | 6/1984 | |
| EP | 0303477 | 2/1989 | |
| EP | 0826376 A1 | 3/1998 | |
| EP | 0877603 | 11/1998 | |
| GB | 929210 | 6/1963 | |
| WO | 8803755 | 6/1988 | |
| WO | 9203927 | 3/1992 | |
| WO | 94/26113 | 11/1994 | |
| WO | 9628023 | 9/1996 | |
| WO | 96/33611 A2 | 10/1996 | |
| WO | 9639842 | 12/1996 | |
| WO | 9905250 | 2/1999 | |
| WO | 99/39576 A1 | 8/1999 | |
| WO | 0042990 | 7/2000 | |
| WO | 0145513 | 6/2001 | |
| WO | 03/003831 A1 | 1/2003 | |
| WO | 03/030644 A1 | 4/2003 | |
| WO | 2004/016252 A1 | 2/2004 | |
| WO | 2004/043147 A1 | 5/2004 | |
| WO | 2004/095926 | 11/2004 | |
| WO | 2005/013714 A1 | 2/2005 | |
| WO | 2005/072695 A1 | 8/2005 | |
| WO | 2006/089747 A2 | 8/2006 | |
| WO | 2007/031565 A2 | 3/2007 | |
| WO | 2007/053760 A2 | 5/2007 | |
| WO | 2007/126915 A1 | 11/2007 | |
| WO | 2008/032328 A2 | 3/2008 | |
| WO | WO2008/032328 * | 3/2008 | A01N 25/28 |
| WO | 2008/093347 | 8/2008 | |
| WO | 2008/134819 A1 | 11/2008 | |

OTHER PUBLICATIONS

International Preliminary Report of Patentability; PCT/US2010/001238.

International Preliminary Report of Patentability; PCT/US2010/001240.

International Preliminary Report of Patentability; PCT/US2010/001228.

International Search Report and Written Opinion of the International Searching Authority, PCT/US2010/001238.

Getchell and Bh Subramanyam A I:"Evaluation of a Dry Formulation on Two Extruded Pet Foods for Controlling Four Stored-Product Insects" Biopesticides International, Koul Research Foundation, vol. 3, No. 2, Jan. 1, 2007, pp. 108-116, XP007914136;ISSN; 0973-483X; abstract "Pet Foods" pp. 109 "Treatment of Pet Foods with spinosad"; p. 109-p. 110 "Discussion"; p. 112-p. 114.

Demchak, R. J., et al.: Photostability of Abemectin/Zein Microspheres Journal of Agricultural and Food Chemistry, American Chemical Society. US LNKD-DOI: 10.1021/JF960356N, vol. 45, No. 1, Jan. 1, 1997, pp. 260-262, XP002457256 ISSN: 0021-8561 Introduction; p. 260.

Dog Food Analysis: "Purina One Adult Dog Chicken & Rice Formula" Internet Citation; Mar. 5, 2006, X{007914143 Retrieved from the internet: URL: http//www.dogfoodanalysis.com/dogfood_review/showproduct.php?product=258&cat=7 (retreived on Jul. 27, 2010) the whole document.

International Search Report, Written Opinion, and Preliminary Report of Patentability of the International Searching Authority, PCT/US2006/042912.

Latch, Douglas E., et al.; Aqueous Photochemistry of Triclosan, Formation of 2, 4-dichlorophenol 2, B-dichlorodibenzo-p-dioxin and oligomerization products; Dept. CHem., University of Minnesota; Environmental Toxicology and Chemistry, Mar. 2005, vol. 24, pp. 517-525.

Biebel R., et al.; Action of pyrethrum-based formulations against grain weevils; International Journal of Pharmaceutics; Apr. 30, 2003, vol. 256, pp. 175-181, XP002457258.

Nogueira, Costa G.H., Antiparasitic for Cattle Comprises Two Macrocylclic Lactones with Bensyl alcohol, Tocopherol and Olive Oil; Ins Pesquisa Em Saude Animal Ltda; Aug. 12, 2003.

Clements, Paul et al.; Soil Sensitised Generation of Singlet Oxygen in the Photodegradation of Biorsmethrin; School of Applied Chemistry, Revised manuscript Aug. 12, 1991; accepted Sep. 15, 1991.

Palumbo, Maria C., et al.; on the Mechanism of Quenching of Singlet Oxygen by Chlorinated Phenolic Pesticides; Toxilogical and Environmental Chemistry; vol. 18, pp. 103-116.

Martire, Daniel O., et al.; Singlet Molecular Oxygen [O2(1 Af)] Production and Quenching by Hydrozybiphenyls; Chemosphere, vol. 26, No. 9, pp. 1691-1701, 1993.

* cited by examiner

PESTICIDE COMPOSITIONS EXHIBITING ENHANCED ACTIVITY AND METHODS FOR PREPARING SAME

CROSS REFERENCE TO RELATED APPLICATIONS

The present application is a Divisional of U.S. patent application Ser. No. 12/768,263 filed 27 Apr. 2010, now U.S. Pat. No. 8,796,476, which claims priority to U.S. Provisional Patent Application No. 61/214,989 filed 30 Apr. 2009 and to U.S. Provisional Application No. 61/277,974 filed on 1 Oct. 2009.

FIELD OF THE INVENTION

The inventions disclosed in this document are related to the field of pesticides and their use in controlling pests.

BACKGROUND

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

Many pesticide compositions have been developed over time to destroy pests and alleviate the damages they cause. These compositions are often applied to the environment in which the insects or other pests live or where their eggs are present, including the air surrounding them, the food they eat, or objects which they contact. Several of these compositions are vulnerable to chemical and physical degradation when applied to these environments. If these types of degradation occur, the pesticidal activity of the pesticides can be adversely affected, commonly necessitating an increase in the concentration at which the pesticides are applied and/or more frequent applications of the pesticides. As a result, user costs and the cost to consumers can escalate. Therefore, a need exists for new pesticide compositions that exhibit increased stability and enhanced activity compared to existing pesticide compositions when, for example, the pesticide compositions are applied to an environment to control pests.

SUMMARY OF THE INVENTION

The present invention concerns novel pesticide compositions, methods for preparing the compositions, and their use in controlling insects and certain other invertebrates. In one embodiment, a method includes providing a liquid composition that includes at least one pesticide and at least one co-ingredient that enhances pesticidal activity of the composition compared to a composition dissimilar only in not having the at least one co-ingredient. The at least one co-ingredient includes at least one metal oxide, a combination of at least one transition metal salt and at least one proteinaceous material, or a combination of at least one proteinaceous material and at least one polymeric material. The method further includes spray drying the liquid composition to provide a solid composition which may be, for example, in a powder or granular form. In one form of this method, the at least one pesticide is a macrocyclic lactone insecticide.

In another form of this method, the at least one pesticide is a spinosyn, such as spinetoram or spinosad. However, it should be appreciated that alternatives for the at least one pesticide are contemplated. In one aspect of the method, the liquid composition further includes water and the spray drying includes at least partially dehydrating or drying the liquid composition such that the liquid composition includes a greater percentage of water, by weight, than the solid composition. In yet another aspect of the method, the at least one pesticide and the at least one co-ingredient are present in the liquid composition at a ratio, by weight, that is substantially equivalent to a ratio, by weight, at which the at least one pesticide and the at least one co-ingredient are present in the solid composition. Still, another aspect of the method includes applying to a locus where control is desired an insect-inactivating amount of the solid composition.

In another embodiment, a method includes providing a liquid composition that includes at least one pesticide and at least one co-ingredient that enhances pesticidal activity of the composition compared to a composition dissimilar only in not having the at least one co-ingredient. The method further includes spray drying the liquid composition to provide a solid composition that exhibits enhanced pesticidal activity compared to the liquid composition. In one aspect of this method, the liquid composition includes a ratio by weight between the at least one pesticide and the at least one co-ingredient which is substantially equivalent to a ratio by weight between the at least one pesticide and the at least one co-ingredient in the solid composition. In another aspect of this method, the liquid composition further includes water and the spray drying includes at least partially dehydrating or drying the liquid composition. In a further aspect, the dehydrating or drying includes reducing water from at least about 20% by weight in the liquid composition to less than about 10% by weight in the solid composition. Still, it should be appreciated that further variations in the reduction of water from the liquid composition to the solid composition are contemplated.

In one other embodiment, a method includes providing a liquid composition that includes spinetoram, ferric oxide and a polymeric material that includes polyvinyl pyrrolidone. The method further includes spray drying the liquid composition to provide a solid composition.

In yet another embodiment, a composition includes a solid material including at least one pesticide and at least one co-ingredient that enhances pesticidal activity of the composition compared to a composition dissimilar only in not having the at least one co-ingredient. Additionally, the solid material exhibits enhanced pesticidal activity compared to a liquid composition that includes the at least one pesticide and the at least one co-ingredient in a ratio by weight that is substantially equivalent to a ratio by weight between the at least one pesticide and the at least one co-ingredient in the solid material.

Still, further embodiments, forms, features, aspects, benefits, objects, and advantages of the present invention shall become apparent from the detailed description and examples provided.

DETAILED DESCRIPTION OF THE INVENTION

Throughout this document, all temperatures are given in degrees Celsius, and all percentages are weight percentages unless otherwise stated.

Pesticide compositions exhibiting increased stability and enhanced pesticidal activity are described in this document. More particularly, in one or more embodiments, the pesticide compositions exhibit enhanced residual pesticidal activity. A pesticide is herein defined as any compound which shows some pesticidal or biocidal activity, or otherwise participates in the control or limitation of pest populations. Such compounds include fungicides, insecticides, nematocides, miticides, termiticides, rodenticides, molluscides, arthropodicides, herbicides, biocides, as well as pheromones and attractants and the like.

Examples of pesticides that can be included in the compositions described herein include, but are not limited to, antibiotic insecticides, macrocyclic lactone insecticides (for example, avermectin insecticides, milbemycin insecticides, and spinosyn insecticides), arsenical insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, fumigant insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

Some of the particular insecticides that can be employed in the compositions described in this document include, but are not limited to, the following: 1,2-dichloropropane, 1,3 dichloropropene, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphosmethyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bioresmethrin, bistrifluoron, borax, boric acid, boric acid, bromfenvinfos, bromocyclen, bromo-DDT, bromophos, bromophosethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinoprop, dinosam, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane. eprinomectin, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methylchloroform, methylene chloride, metofluthrin, metolcarb, metoxadiazone, mevinphos, mexacarbate, milbemectin, milbemycin oxime, mipafox, mirex, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin. precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphosmethyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulfluramid, sulfotep, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and α-ecdysone.

Additionally, it is contemplated that any combination of the above insecticides can be employed in the compositions described herein. For more information consult "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council.

Various pesticides are susceptible to chemical and physical degradation in the presence of certain environmental influences, such as heat and/or light. Pesticides that are susceptible to degradation with respect to the latter of these influences are commonly referred to as "photo-labile." With respect to at least some photo-labile pesticides, it is believed that their degradation can be attributed to a reaction with singlet oxygen. Examples of pesticides that are reactive with singlet oxygen include, but are not limited to, certain olefins, aromatics, phenols, naphthols, furans, pyrans and other heterocycles containing oxygen; pyrroles, oxazoles, imidazoles, indoles and other heterocycles containing nitrogen; aliphatic, alicyclic and aromatic amines; amino acids, peptides and proteins; and sulfur containing compounds such as mercaptans and sulfides; and the like. Further details regarding the determination of whether a pesticide is reactive with singlet oxygen are provided in International Patent Publication No. WO 2007/053760. It should be appreciated that any one or combination of the aforementioned photo-labile, singlet oxygen reactive pesticides could be included in the compositions described herein.

More particular examples of photo-labile, singlet oxygen reactive pesticides that could be included either alone or in combination with each other in the compositions described herein include, but are not limited to, natural products which are microorganisms, microbial products, and materials derived or extracted from plants, animals, or mineral-bearing rocks. These natural products include products derived from naturally derived soil dwelling organisms such as actinomycete bacteria such as, for example, macrocyclic lactone insecticides. One exemplary macrocyclic lactone insecticide includes avermectins and derivatives thereof, such as abamectin, doramectin, emamectin, eprinomectin, ivermectin and selamectin. Another exemplary macrocyclic lactone insecticide includes milbemycins and derivatives thereof, such as lepimectin, milbemectin, milbemycin oxime and moxidectin. Yet another exemplary macrocyclic lactone insecticide includes spinosyns, such as spinosad, and derivatives thereof such as synthetically produced spinetoram as disclosed in U.S. Pat. Nos. 5,227,295; 5,670,364; 5,591,606; 6,001,981; 6,143,526; 6,455,504; 6,585,990; 6,919,464; 5,362,634; 5,539,089; and 5,202,242, each of which is hereby incorporated herein by reference in its entirety. Other natural products include sabadilla or veratrine, pyrethrum or pyrethrin, neem oil or azadirachtin, rotenone, ryania or ryanodine, *Bacillus thuringiensis* (B. t.), *Bacillus subtilis*, pheromones, natural attractants and the like. Other pesticides that could be included in the compositions described herein can include synthetically produced pesticides which are reactive toward singlet oxygen. Examples include, but are not limited to indoxacarb, imazalil and fenpropimorph. In addition to the foregoing, it should be appreciated that the compositions described herein could also include at least one pesticide which is photo-labile or reactive with singlet oxygen and at least one other pesticide which is not reactive with singlet oxygen or otherwise photo-labile.

Compositions that include at least one or a mixture of the aforementioned pesticides and at least one co-ingredient that enhances the pesticidal activity of the composition compared to a composition dissimilar only in not having the at least one co-ingredient have recently been discovered. For example, it is contemplated that the activity or half-life of the composition is extended and therefore the same activity can be achieved with a lower amount of the composition when compared to a composition dissimilar only in not having the at least one co-ingredient. Additionally or alternatively, it is contemplated that improved pesticidal control over time is achieved with the composition including the at least one co-ingredient when compared to a composition dissimilar only in not having the at least one co-ingredient.

In one embodiment, the at least one co-ingredient includes at least one metal oxide and the composition exhibits enhanced pesticidal activity compared to a composition dissimilar only in not having the metal oxide. As used herein, the term "metal oxide" is used to describe a compound containing at least one oxygen atom and at least one metal atom. In one form, the metal oxide is insoluble in water. Additionally or alternatively, it is contemplated that the metal oxide may be a transition metal oxide. Non-limiting examples of transition metal oxides include zinc oxide; an iron oxide, such as ferrous (iron (II) oxide) or ferric (iron (III) oxide) oxide as well as iron (II, III) oxide; a copper oxide, such as cuprous (copper (I) oxide) or cupric (copper (II) oxide) oxide; a titanium oxide, such as titanium dioxide (titanium (IV) oxide), titanium (II) oxide and titanium (III) oxide; a cobalt oxide, such as cobalt (II) oxide and cobalt (III) oxide; a nickel oxide, such as nickel (II) oxide or nickel (III) oxide; a manganese oxide, such as manganese (II, III) oxide; a chromium oxide, such as chromium (III) oxide or chromium (IV) oxide; silver oxide; palladium oxide; and lanthanum oxide. In one or more forms, the metal oxide may also be a hydroxide or part of a hydrate complex. Examples of these include zinc hydroxide, partially dehydrated zinc hydroxide or zinc oxide hydroxide, iron (II) hydroxide, iron (III) hydroxide, iron oxide hydroxide, anhydrous or hydrated iron oxide and iron oxide hydroxide, manganese hydroxide, manganese oxide hydroxide, hydrated manganese hydroxide or manganese oxide hydroxide, copper hydroxide, partially dehydrated copper hydroxide or copper oxide hydroxide, titanium hydroxide, titanium oxide hydroxide, hydrated titanium hydroxide or titanium oxide hydroxide, just to provide a few possibilities. It should be appreciated that a combination of one or more of the aforementioned metal oxides can be employed in the compositions described herein. In one particular form, the metal oxide is selected from the group consisting of zinc oxide, ferric oxide, cupric oxide, titanium dioxide and mixtures thereof.

The metal oxide is typically present within the composition of this embodiment in an activity enhancing amount. An activity enhancing amount is an amount which increases the half life of the composition, or alternatively will enable the composition to achieve the same control of pests at a level which is less than the amount required for the same pesticidal protection or control of the composition in the absence of the metal oxide. In other words, the metal oxide will either reduce the rate required for protection or extend the residuality of the composition.

In another embodiment, the at least one co-ingredient includes at least one metal oxide and at least one proteinaceous material. It should be appreciated that the metal oxide in this embodiment can be one or a mixture of those examples identified above. As used herein, the term "proteinaceous material" is used to describe a material, composition or compound that is defined by a protein, includes at least one protein or is a basic element of a protein. In one form, the proteinaceous material includes a water-soluble protein. Further non-limiting examples of proteinaceous materials include albumin, such as egg albumen or bovine serum albumin (BSA); casein; gelatin; zein; a whey composition, such as a mixture of lactose and whey protein; whey protein and amino acids such as cysteine, methionine, trytophan, histidine, tyrosine, arginine, lysine, glutamine, glutamic acid, cystine, serine and asperigine, just to name a few possibilities. It is also contemplated that the co-ingredient could include two or more of the foregoing non-limiting examples of the proteinaceous material. In one aspect of this embodiment, the composition exhibits enhanced pesticidal activity compared to a composition dissimilar only in not having the at least one metal oxide and the at least one proteinaceous material.

The at least one metal oxide and the at least one proteinaceous material are typically present within the composition of this embodiment in an activity enhancing amount. An activity enhancing amount is an amount which increases the half life of the composition, or alternatively will enable the composition to achieve the same control of pests at a level which is less than the amount required for the same pesticidal protection or control of the composition in the absence of the metal oxide and the proteinaceous material. In other words, the metal oxide and the proteinaceous material will either reduce the rate required for protection or extend the residuality of the composition.

In yet another embodiment, the at least one co-ingredient includes at least one metal oxide and at least one polymeric material. In this embodiment, it should be appreciated that the metal oxide can be one or more of those examples identified above. As used herein, the term "polymeric material" is used to describe a material, compound or composition that is defined by or includes at least one polymer or a derivative thereof. In one non-limiting example, the polymeric material includes polyvinyl alcohol. In other examples, the polymeric material may include: a derivative of polyvinyl alcohol; polyvinyl pyrolidone and/or one or more derivatives thereof; natural or synthetic latexes; a polysaccharide and/or one or more derivatives thereof, or polyvinyl acetate and/or one or more derivatives thereof. In one specific example, the polymeric material may be a high molecular weight vinyl-acrylic latex, such as UCAR™ Latex 379G commercially available from The Dow Chemical Company, 2030 Dow Center, Midland, Mich. 48674. In another specific example, the polymeric material may be a terpene polymer, such as NU FILM 17® commercially available from Miller Chemical and Fertilizer Corporation, P.O. Box 333, 120 Radio Road, Hanover, Pa. 17331. In still another example, the polymeric material may be a polysaccharide or a modified polysaccharide such as starch, including water-soluble starches, potato starch and other processed starches, chitosan or methyl cellulose. In another example, the polymeric material may be a hypromellose polymer, such as METHOCEL™ K4M commercially available from The Dow Chemical Company. It should also be appreciated that the co-ingredient could include two or more of the foregoing non-limiting examples of the polymeric material. In one aspect of this embodiment, the composition exhibits enhanced pesticidal activity compared to a composition dissimilar only in not having the at least one metal oxide and the at least one polymeric material.

The at least one metal oxide and the at least one polymeric material are typically present within the composition of this embodiment in an activity enhancing amount. An activity enhancing amount is an amount which increases the half life of the composition, or alternatively will enable the composition to achieve the same control of pests at a level which is less than the amount required for the same pesticidal protection or control of the composition in the absence of the metal oxide and the polymeric material. In other words, the metal oxide and the polymeric material will either reduce the rate required for protection or extend the residuality of the composition.

In still another embodiment, the at least one co-ingredient includes at least one metal oxide, at least one proteinaceous material and at least one polymeric material. In this particular embodiment, it should be appreciated that the metal oxide, proteinaceous material and polymeric material can be one or more of those examples respectively identified above for each. In one aspect of this embodiment, the composition exhibits enhanced pesticidal activity compared to a composition dissimilar only in not having the metal oxide, proteinaceous material and polymeric material.

The at least one metal oxide, at least one proteinaceous material and at least one polymeric material are typically present within the composition of this embodiment in an activity enhancing amount. An activity enhancing amount is an amount which increases the half life of the composition, or alternatively will enable the composition to achieve the same control of pests at a level which is less than the amount required for the same pesticidal protection or control of the composition in the absence of the metal oxide, proteinaceous material and polymeric material. In other words, the metal oxide, proteinaceous material and polymeric material will either reduce the rate required for protection or extend the residuality of the composition.

In yet another embodiment, the at least one co-ingredient includes at least one proteinaceous material and at least one polymeric material. In this particular embodiment, it should be appreciated that the at least one proteinaceous material and the at least one polymeric material can be one or more of those examples respectively identified above for each. In one aspect of this embodiment, the composition exhibits enhanced pesticidal activity compared to a composition dissimilar only in not having the proteinaceous material and the polymeric material.

The at least one proteinaceous material and the at least one polymeric material are typically present within the composition of this embodiment in an activity enhancing amount. An activity enhancing amount is an amount which increases the half life of the composition, or alternatively will enable the composition to achieve the same control of pests at a level which is less than the amount required for the same pesticidal protection or control of the composition in the absence of the proteinaceous material and the polymeric material. In other words, the proteinaceous material and the polymeric material will either reduce the rate required for protection or extend the residuality of the composition.

In another embodiment, the at least one co-ingredient includes at least one polymeric material. The polyermic material may be one or a mixture of more than one of the polymeric materials described above and is typically present within the composition of this embodiment in an activity enhancing amount. An activity enhancing amount is an amount which increases the half life of the composition, or alternatively will enable the composition to achieve the same control of pests at a level which is less than the amount required for the same pesticidal protection or control of the composition in the absence of the polymeric material. In other words, the polymeric material will either reduce the rate required for protection or extend the residuality of the composition.

In still another embodiment, the at least one co-ingredient includes at least one metal salt and at least one proteinaceous material. In this embodiment, the composition exhibits enhanced pesticidal activity compared to a composition dissimilar only in not having the metal salt and the proteinaceous material. As used herein, the term "metal salt" refers to a compound in which the hydrogen(s) of an acid is(are) replaced by a metal while retaining the same organic or inorganic moiety as the acid. By way of non-limiting example, organic and inorganic moieties that can form part of a metal salt include acetate, acetylacetonate, nitrate, sulfate, carbonate and halides, such as chloride, bromide, fluoride and iodide.

In one or more forms, the metal salt can be a transition metal salt. Non-limiting examples of transition metal salts include transition metal acetates, transition metal acetylacetonates, transition metal nitrates, transition metal sulfates, transition metal carbonates and transition metal halides, including chlorides, fluorides, bromides and iodides. More particular examples of transition metal acetates include, but are not limited to, zinc acetate, ferrous (iron (II)) acetate, ferric (iron (III)) acetate, cobalt (II) acetate and cupric (copper (II)) acetate. For transition metal acetylacetonates, more particular but non-limiting examples include cuprous (copper (I)) acetylacetonate, cupric (copper (II)) acetylacetonate, nickel (II) acetylacetonate and zinc acetylacetonate. More particular examples of transition metal nitrates include, but are not-limited to, zinc nitrate, cupric (copper (II)) nitrate, manganese (III) nitrate, ferric (iron (III)) nitrate, cobalt (III) nitrate and nickel (II) nitrate. Non-limiting examples of transition metal sulfates include zinc sulfate, ferrous (iron (II)) sulfate, ferric (iron (III)) sulfate, manganese (II) sulfate, cobalt (II) sulfate, nickel (II) sulfate, and cupric (copper (II)) sulfate. A few particular but non-limiting examples of transition metal carbonates include zinc carbonate, manganese (II) carbonate, iron carbonate, nickel (II) carbonate, cobalt (II) carbonate and cupric (copper (II)) carbonate. More particular examples of transition metal fluorides include, but are not limited to, cuprous (copper (I)) fluoride, cupric (copper (II)) fluoride, zinc fluoride, manganese (II) fluoride, manganese (III) fluoride and ferric (iron (III)) fluoride. Non-limiting examples of transition metal chlorides include zinc chloride, cuprous (copper (I)) chloride, cupric (copper (II)) chloride, manganese (II) chloride, nickel (II) chloride, cobalt (II) chloride, ferrous (iron (II)) chloride and ferric (iron (III)) chloride. With respect to transition metal bromides, a few examples include, but are not limited to, zinc bromide, cuprous (copper (I)) bromide, cupric (copper (II)) bromide, cobalt (II) bromide, ferrous (iron (II)) bromide, ferric (iron (II)) bromide, manganese (II) bromide and nickel (II) bromide. A few more particular but non-limiting examples of transition metal iodides include manganese (II) iodide, nickel (II) iodide, cuprous (copper (I)) iodide and zinc iodide. Additionally, it is contemplated that the at least one co-ingredient could include any combination of the above transition metal salts.

In another form of this embodiment, it is contemplated that the at least one transition metal salt is water soluble. Non-limiting examples of water-soluble transition metal salts include zinc chloride, zinc iodide, zinc nitrate, zinc bromide, zinc sulfate, zinc acetate, cupric (copper (II)) chloride, cupric (copper II)) bromide, cuprous (copper (I)) bromide, cupric (copper (II)) nitrate, cupric (copper (II)) acetate, nickel (II) nitrate, nickel (II) bromide, nickel (II) chloride, nickel (II) iodide, nickel (II) sulfate, cobalt (II) nitrate, cobalt (II) sulfate, cobalt (II) acetate, cobalt (II) bromide, cobalt (II) chloride, ferrous (iron (II)) chloride, ferric (iron (III)) chloride, ferrous (iron (II)) sulfate, ferric (iron (III)) sulfate, ferrous (iron (II)) acetate, ferric (iron (III)) nitrate, ferrous (iron (II)) bromide, manganese (II) sulfate and manganese (II) chloride.

The at least one metal salt and the at least one proteinaceous material are typically present within the composition of this embodiment in an activity enhancing amount. An activity enhancing amount is an amount which increases the half life of the composition, or alternatively will enable the composition to achieve the same control of pests at a level which is less than the amount required for the same pesticidal protection or control of the composition in the absence of the metal salt and the proteinaceous material. In other words, the metal salt and the proteinaceous material will either reduce the rate required for protection or extend the residuality of the composition.

Further details and examples of the above-described compositions may be found in U.S. patent application Ser. Nos. 12/768,057, 12/767,970, and 12/768,084, each of which is entitled “PESTICIDE COMPOSITIONS EXHIBITING ENHANCED ACTIVITY” and was filed on the same date as the subject application. The contents of each of these applications are hereby incorporated herein by reference in their entirety.

The compositions described above can be prepared and provided in any suitable manner and also include other components, further details of which will be provided below. In one exemplary form, the pesticide, the at least one co-ingredient that enhances the pesticidal activity of the pesticide, water and any other components, if present, are mixed together, homogenized and provided as a liquid composition. It has now been surprisingly discovered that the liquid composition can be spray dried to provide a solid composition that exhibits enhanced pesticidal activity relative to the liquid composition. The solid composition may be in a powder or granular form, just to provide a few non-limiting possibilities.

As will be appreciated by those skilled in the art, various parameters of the spray drying process, including feed rate, nozzle pressure, inlet temperature and outlet temperature amongst other possibilities, may be adjusted for each process performed. For example, in one non-limiting form, it is contemplated that a spray drying process may utilize a feed rate between about 200 and about 500 ml/hr, a nozzle pressure between about 2 bar and about 8 bar, an inlet temperature between about 95° C. and about 180° C. and an outlet temperature between about 30° C. and about 120° C. In another non-limiting form, it is contemplated that a spray drying process may utilize a feed rate between about 250 and about 450 ml/hr, a nozzle pressure between about 3 bar and about 7 bar, an inlet temperature between about 105° C. and about 50° C. and an outlet temperature between about 40° C. and about 110° C. In yet another embodiment, it is contemplated that a spray drying process may utilize a feed rate from about 300 to about 400 ml/hr, a nozzle pressure from about 4 bar to about 6 bar, an inlet temperature from about 115° C. to about 140° C. and an outlet temperature from about 50° C. to about 100° C. However, additional values for the feed rate, nozzle pressure, inlet temperature and outlet temperature at which the spray drying process is performed are contemplated. Moreover, it should also be appreciated that the parameters utilized during the spray drying process will be dependent on the specific formulation of each composition and limited by the upper and lower degradation limits of the ingredients included in each composition being spray dried.

During the spray drying, the liquid composition is at least partially dehydrated or dried, with such dehydration or dyring resulting in the conversion of the liquid composition to the solid composition which includes a smaller percentage by weight of water than the liquid composition. In one or more forms, the spray drying will remove all or substantially all of the water from the liquid composition as it is converted to the solid composition. However, it should be appreciated that residual water may be present in one or more forms of the solid composition.

In one form, the spray drying reduces water from at least about 20% by weight in the liquid composition to less than about 15% by weight in the solid composition. In yet another form, the spray drying reduces water from at least about 40% by weight in the liquid composition to less than about 10% by weight in the solid composition. In still another form, the spray drying reduces water from at least about 50% by weight in the liquid composition to less than about 5% by weight in the solid composition. In another form, the spray drying reduces water from at least about 50% by weight in the liquid composition to between about 0.001% to about 2% by weight of water in the solid composition. Still, alternative values for the amount of water that is reduced from the liquid composition to the solid composition are contemplated. For example, in another form the spray drying reduces water from between about 20% to about 90% by weight in the liquid composition to between about 0.001 to about 15% by weight in the solid composition.

In another form, the solid composition includes between about 0.001% to about 20% by weight of water after the spray drying. In yet another form, the solid composition includes from about 0.001% to about 15% by weight of water after the spray drying. In still another form, the solid composition includes from about 0.001% to about 10% by weight of water after the spray drying. In another form, the solid composition includes from about 0.001% to about 5% by weight of water after the spray drying. In yet another form, the solid composition includes from about 0.001% to about 4% by weight of water after the spray drying. Still, in another form the solid composition includes from about 0.001% to about 2% by weight of water after the spray drying. In another form, the solid composition includes from about 0.001% to about 1% by weight of water after the spray drying. However, it should be appreciated that alternatives values for the weight percentage of water in the solid composition after the spray drying are contemplated.

While not previously mentioned, any other volatile materials besides water, if present in the liquid composition, will typically be entirely or substantially removed as the liquid composition is converted to the solid composition during the spray drying. However, it is contemplated that residual volatile materials other than water could be present in the solid composition after the spray drying. Additionally, the pesticide and the at least one co-ingredient that enhances the pesticidal activity of the composition are generally not volatile and will generally not be affected by the spray drying. Thus, it should be appreciated that the solid composition after spray drying will include a ratio by weight between the pesticide and the at least one co-ingredient that is the same as or substantially equivalent to the ratio by weight between the pesticide and the at least one co-ingredient in the liquid composition.

Pests

In one or more additional embodiments, the invention disclosed in this document can be used to control pests.

In one embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass *Ataenius*), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae. Hylobius pales* (pales weevil), *Hypera* spp. (weevils), *Hypera postica* (alfalfa weevil), *Hyperdoes* spp. (*Hyperodes* weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti. Megascelis* spp., *Melanotus communis, Meligethes* spp., *Meligethes aeneus* (blossom beetle), *Melolontha melolontha* (common European cockchafer), *Oberea brevis, Oberea linearis, Orvctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana. Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (Eurpoean chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennyhlvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cochliomyvia* spp. (screwworms), *Contarinia* spp. (Gall midges), *Culex* spp. (mosquitoes), *Dasineura* spp. (gall midges), *Dasineura brassicae* (cabbage gall midge), *Delia* spp. *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomya* spp. (leafminer flies), *Liriomvza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (fit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella. Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi. Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leathoppers), *Eriosoma lanigerum* (woolly apple aphid), *Icerya purchasi* (cottony cushion scale), *Idioscopus nitidulus* (mango leathopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leathoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites). *Incistitermes* spp. (drywood termites), *Macrotermes* spp. (fungus growing termites), *Marginitermes* spp. (drywood termites), *Microcerotermes* spp. (harvester termites), *Microtermes obesi. Procornitermes* spp. *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp. and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata. Adoxophyes* spp., *Adoxophyes orana, Agrotis* spp. (cutworms), *Agrotis ipsilon* (black cutworm), *Alabama argillacea* (cotton leafworm), *Amorbia cuneana. Amyelosis transitella* (navel orangeworm), *Anacamptodes defectaria, Anarsia lineatella* (peach twig borer), *Anomis sabulijera* (jute looper), *Anticarsia gemmatalis* (velvetbean caterpillar), *Archips argyrospila* (fruit tree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leaf perforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (oblique banded leaf roller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema. Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus. Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa. Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana. Spodoptera* spp. (armyworms), *Spodoptera exigua* (beet armyworm), *Spodoptera fugiperda* (fall armyworm), *Spodoptera oridania* (southern armyworm), *Svnanthedon* spp. (root borers), *Thecla basilides, Thermisia gemmatalis, Tineola bisselliella* (webbing clothes moth), *Trichoplusia ni* (cabbage looper), *Tuta absoluta. Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen house).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria. Melanoplus* spp. (grasshoppers), *Microcentrum retinerve* (angular winged katydid), *Pterophylla* spp. (kaydids), *chistocerca gregaria. Scudderia furcata* (fork tailed bush katydid), and *Valanga nigricorni.*

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (thrips). A non-exhaustive list of these pests includes, but is not limited to, *Frankliniella fusca* (tobacco thrips), *Frankliniella occidentalis* (western flower thrips), *Frankliniella shultzei Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma*

*americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranvcus* spp., *Eotetranychus carpini* (yellow spider mite), *Epitimerus* spp., *Eriophyes* spp., *Ixodes* spp. (ticks), *Metatetranycus* spp., *Notoedres cati. Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

For more detailed information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Mixtures

The compositions disclosed in this document can also be used, for reasons of economy and synergy, with acaricides, algicides, antifeedants, avicides, bactericides, bird repellents, chemosterilants, fungicides, herbicide safeners, herbicides, insect attractants, insect repellents, mammal repellents, mating disrupters, molluscicides, other insecticides, other pesticides, plant activators, plant growth regulators, rodenticides, synergists, defoliants, desiccants, disinfectants, semiochemicals, and virucides (these categories not necessarily mutually exclusive).

Formulations

The compositions described in this document may also be provided with a phytologically-acceptable inert carrier and can be formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "CATALOGUE OF PESTICIDE FORMULATION TYPES AND INTERNATIONAL CODING SYSTEM" Technical Monograph no 2, 5th Edition by CropLife International (2002).

Pesticide compositions can be frequently applied as aqueous suspensions or emulsions prepared from concentrated formulations of such compositions. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide composition, a carrier, and surfactants. The carrier is usually chosen from among the attapulgite clays, the montmorillonite clays, the diatomaceous earths, or the purified silicates. Effective surfactants, which can comprise from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates comprise a convenient concentration of a pesticide composition dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticide compositions dispersed in an aqueous carrier. Suspensions are prepared by finely grinding the pesticide composition and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide composition at the same time by preparing the aqueous mixture and homogenizing it in an implement such as a sand mill, ball mill, or piston-type homogenizer.

Pesticide compositions may also be applied as granular formulations that are particularly useful for applications to the soil. Granular formulations contain the pesticide composition dispersed in a carrier that comprises clay or a similar substance. Such formulations are usually prepared by dissolving the pesticide composition in a suitable solvent and applying it to a granular carrier which has been pre-formed to the appropriate particle size, in the range of from about 0.5 to 3 mm. Such formulations may also be formulated by making a dough or paste of the carrier and pesticide composition and crushing and drying to obtain the desired granular particle size.

Dusts containing a pesticide composition are prepared by intimately mixing the pesticide composition in powdered form with a suitable dusty agricultural carrier, such as kaolin clay, ground volcanic rock, and the like. Dusts can be applied as a seed dressing, or as a foliage application with a dust blower machine.

It is equally practical to apply a pesticide composition in the form of a solution in an appropriate organic solvent, usually petroleum oil, such as the spray oils, which are widely used in agricultural chemistry.

Pesticide compositions can also be applied in the form of an aerosol formulation. In such formulations, the pesticide composition is dissolved or dispersed in a carrier, which is a pressure-generating propellant mixture. The aerosol formulation is packaged in a container from which the mixture is dispensed through an atomizing valve.

Pesticide baits are formed when the pesticide composition is mixed with food or an attractant or both. When the pests eat the bait they also consume the pesticide composition. Baits may take the form of granules, gels, flowable powders, liquids, or solids. They may be used in or around pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Oil solution concentrates are made by dissolving a pesticide composition in a solvent that will hold the pesticide composition in solution. Oil solutions of a pesticide composition usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "INSECT PEST MANAGEMENT" 2nd Edition by D. Dent, copyright CAB International (2000). Additionally, for more detailed information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Other Formulation Components

Generally, when the compositions disclosed in this document are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylaryl-ethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alky ethoxylates; linear aliphatic alcohol ethoxylates; aliphatic amine ethoxylates.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information see "CHEMISTRY AND TECHNOLOGY OF AGROCHEMICAL FORMULATIONS" edited by D. A. Knowles, copyright 1998 by Kluwer Academic Publishers. Also see "INSECTICIDES IN AGRICULTURE AND ENVIRONMENT—RETROSPECTS AND PROSPECTS" by A. S. Perry, I. Yamamoto, I. Ishaaya, and R. Perry, copyright 1998 by Springer-Verlag.

Applications

The actual amount of a pesticide composition to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide composition is applied can be any locus inhabited by a pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated in or around a locus; or pests are exterminated, in whole or in part, in or around a locus. Of course a combination of these results can occur. Generally, pest populations, activity, or both are desirably reduced more than fifty percent, preferably more than 90 percent.

Generally, with baits, the baits are placed in the ground where, for example, termites can come into contact with the bait. Baits can also be applied to a surface of a building, (horizontal, vertical, or slanted, surface) where, for example, ants, termites, cockroaches, and flies, can come into contact with the bait.

Because of the unique ability of the eggs of some pests to resist pesticide compositions repeated applications may be desirable to control newly emerged larvae.

Systemic movement of pesticides in plants may be utilized to control pests on one portion of the plant by applying the pesticide composition to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping. Compositions are applied in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide composition can be used or sold commercially, such composition undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

EXAMPLES

The following examples are for illustration purposes and are not to be construed as limiting the invention disclosed in this document to only the embodiments disclosed in these examples.

Example Compositions

Example compositions A-H described below each include spinetoram. Spinetoram is a mixture of 50-90% (2R,3aR, 5aR,5bS,9S,13S,14R,16aS,16bR)-2-(6-deoxy-3-O-ethyl-2, 4-di-O-methyl-α-L-mannopyranosyloxy)-13-[(2R,5S,6R)-5-(dimethylamino)tetrahydro-6-methylpyran-2-yloxy]-9-ethyl-2,3,3a,4,5,5a,5b,6,9,10,11,12,13,14,16a, 16b-hexadecahydro-14-methyl-1H-as-indaceno[3,2-d] oxacyclododecine-7,15-dione and 50-10% (2R,3aR,5aS, 5bS,9S,13S,14R,16aS,16bS)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13,14,16a, 16b-tetradecahydro-4,4-dimethyl-1H-as-indaceno[3,2-d] oxacyclododecine-7,15-dione. Spinetoram is synthetically derived from a natural product and is typically accompanied by various impurities. Accordingly, for each of the compositions prepared below in Examples A-H, an assay was performed on the spinetoram used to determine the presence of impurities.

For each assay, a calibration stock solution sample was prepared by adding approximately 43 mg of an analytically standard form of spinetoram with 10.0 mL of purified water into a 125 mL glass jar. The glass jar was gently swirled until the spinetoram was dispersed into the purified water. 100.0 mL of methanol was then added to the water/spinetoram mixture in the glass jar. A second solution was prepared by adding 10 mL of purified water and approximately 50 mg of the spinetoram product used in each of Examples A-H to a 125 mL glass jar. The glass jar was gently swirled until the spinetoram dispersed into the purified water. 100.0 mL of methanol was then added to the mixture. Each sample was then analyzed using liquid chromatography performed with the following instrumentation and under the following conditions:

Chromatograph: Agilent (formally Hewlett Packard) model 1100 or equivalent
Column: Phenomenex Luna, C8(2) 3 μm, 150 m×4.6 mm column
Mobile Phase A: water with 2 g/L ammonium acetate, pH adjusted to 5.5 with acetic acid
Mobile Phase B: acetonitrile/methanol (80:20, v:v)
Isocratic elution: 20% A/80% B
Flow: 1.0 mL/minute
Injection volume: 10.0 μL
Detector: UV 250 nm
Run Time: 20 minutes
Integrator: Agilent EZChrom Elite data acquisition system, or equivalent Based on the results of the liquid chromatography, the weight percentage of the pure spinetoram component of each of the spinetoram products used in Examples A-H was calculated. The weight percentage of impurities was then calculated by subtracting the weight percentage of the pure spinetoram component from 100. The weight percentage of spinetoram impurities in each of Examples A-H, based from these calculations, is provided below.

Example A

A liquid composition including spinetoram, zinc oxide and egg albumen, among other ingredients, was prepared according to the following. Spinetoram, Reax® 88A, a dispersant commercially available from MeadWestvaco Corporation, P.O. Box 118005, Charleston, S.C. 29423, Geropon® SDS, a surfactant commercially available from Rhodia, Inc., 8 Cedar Brook Drive, Cranbury, N.J. 08512 and a balance of water to provide a suspension concentrate having 25-50% w/w of spinetoram were mixed together. The resulting mixture was milled in an Eiger Mini Motormill media mill to a particle size of 1-10 μm (volume weighted mean diameter). The particle size was measured using a Malvern Mastersizer 2000 laser diffraction particle analyzer. After milling, Nanox® 500, a zinc oxide product commercially available from Elementis Specialties, Inc., P.O. Box 700, 329 Wyckoffs Mill Road, Hightstown, N.J. 08520, and egg albumen from Grade II chicken egg whites from Sigma Aldrich Corporation, 3050 Spruce St., St. Louis, Mo. 63103, were added to the mixture under agitation. The total solids concentration of the mixture was adjusted in the range of 20-50% by weight by adding water. The mixture was then homogenized with a Silverson L4RT-A homogenizer for about 15-30 minutes. The weight percentages for the foregoing ingredients, calculated by comparing the weight of each respective ingredient relative to the total weight of the liquid composition, are provided in Table 1. Table 1 also provides the weight percentage of spinetoram impurities in the liquid composition based on the values determined by the assay procedure described above.

TABLE 1

| Example A | |
|---|---|
| Ingredients | Wt. % |
| Spinetoram | 3.11 |
| Spinetoram impurities | 0.64 |
| Egg Albumen | 15.86 |
| ZnO | 10.09 |
| Reax ® 88A | 1.13 |
| Geropon ® SDS | 0.23 |
| Water | 68.94 |

The liquid composition of Example A was later used for bio-efficacy experiments, but an assay was performed beforehand to determine its proportion by weight of pure spinetoram so appropriate concentrations for testing could be prepared. For this assay procedure, a calibration stock solution sample was prepared by adding approximately 43 mg of an analytically standard form of spinetoram with 10.0 mL of purified water into a 125 mL glass jar. The glass jar was gently swirled until the spinetoram was dispersed into the purified water. 100.0 mL of methanol was then added to the water/spinetoram mixture in the glass jar. A second solution was prepared by adding 10 mL of purified water and approximately 130 mg of the liquid composition to a 125 mL glass jar. The glass jar was gently swirled until the composition dispersed into the purified water. 100.0 mL of methanol was then added to the mixture and the mixture was shaken for at least about 5 minutes on a mechanical shaker. An aliquot of the mixture was then filtered through a 0.45 μm nylon syringe filter, with the first few filtered drops being discarded, and the remaining filtrate providing a sample for liquid chromatography. Each sample was then analyzed using liquid chromatography performed with the following instrumentation and under the following conditions:

Chromatograph: Agilent (formally Hewlett Packard) model 1100 or equivalent
    Column: Phenomenex Luna, C8(2) 3 μm, 150 m×4.6 mm column
    Mobile Phase A: water with 2 g/L ammonium acetate, pH adjusted to 5.5 with acetic acid
    Mobile Phase B: acetonitrile/methanol (80:20, v:v)
    Isocratic elution: 20% A/80% B
    Flow: 1.0 mL/minute
    Injection volume: 10.0 μL
    Detector: UV 250 nm
    Run Time: 20 minutes
    Integrator: Agilent EZChrom Elite data acquisition system, or equivalent Based on the results of the liquid chromatography, the weight percentage of the pure spinetoram component for the liquid composition of Example A was calculated to be 3.1%.

Example B

A portion of the liquid composition prepared in Example A was spray-dried using a Buchi® Model 190 bench top spray dryer from Buchi Corporation, 19 Lukens Drive, Suite 400, New Castle, Del. 19720, at about a 300-400 ml/hr feed rate, 4-6 bar nozzle pressure, 115-140° C. inlet temperature and 50-100° C. outlet temperature to provide Example B as a solid composition. It is believed that the spray drying process removes all or substantially all of the water and other volatile ingredients from the liquid composition of Example A as it is converted to the solid composition of Example B. Since none of the ingredients in the liquid composition of Example A apart from the water is believed to be volatile, the weight percentages for each of the ingredients in the solid composition of Example B were determined on the basis of all water being removed from the liquid composition of Example A during the spray drying. These weight percentages are set forth in Table 2.

TABLE 2

Example B

| Ingredients | Wt. % |
|---|---|
| Spinetoram | 10.0 |
| Spinetoram impurities | 2.05 |
| Egg Albumen | 51.08 |
| ZnO | 32.5 |
| Reax ® 88A | 3.64 |
| Geropon ® SDS | 0.73 |

Since the solid composition of Example B was later used for bio-efficacy experiments, an assay was performed to determine its proportion by weight of pure spinetoram so appropriate concentrations for testing could be prepared. For this assay procedure, a calibration stock solution sample was prepared by adding approximately 43 mg of an analytically standard form of spinetoram with 10.0 mL of purified water into a 125 mL glass jar. The glass jar was gently swirled until the spinetoram was dispersed into the purified water. 100.0 mL of methanol was then added to the water/spinetoram mixture in the glass jar. A second solution was prepared by adding 10 mL of purified water and approximately 130 mg of the solid composition of Example B to a 125 mL glass jar. The glass jar was gently swirled until the solid composition dispersed into the purified water. 100.0 mL of methanol was then added to the mixture and the mixture was shaken for at least about 5 minutes on a mechanical shaker. An aliquot of the mixture was then filtered through a 0.45 μm nylon syringe filter, with the first few filtered drops being discarded, and the remaining filtrate providing a sample for liquid chromatography. Each sample was then analyzed using liquid chromatography performed with the instrumentation and in accordance with the parameters set forth above in Example A. Based on the results of the liquid chromatography, the weight percentage of the pure spinetoram component for the solid composition of Example B was calculated to be 11.4%.

Example C

A liquid composition including spinetoram, egg albumen and polyvinyl alcohol, among other ingredients, was prepared according to the following. Spinetoram, Reax® 88A, Geropon® SDS and a balance of water to provide a suspension concentrate having 25-50% w/w of spinetoram were mixed together. The resulting mixture was milled in an Eiger Mini Motormill media mill from Eiger Machinery, Inc. to a particle size of 1-10 μm (volume weighted mean diameter). The particle size was measured using a Malvern Mastersizer 2000 laser diffraction particle analyzer from Malvern Instruments Ltd. After milling, egg albumen from Grade II chicken egg whites from Sigma Aldrich Corporation and a 15% w/w aqueous solution of Celvol® 205 polyvinyl alcohol from Celanese Corporation, 1601 West LBJ Freeway, Dallas, Tex., 75234, were added to the mixture under agitation. The 15% w/w aqueous solution of Celvol® 205 polyvinyl alcohol was prepared according to manufacturer instructions. The total solids concentration of the mixture was adjusted in the range of 20-50% by weight by adding water. The mixture was then homogenized with a Silverson L4RT-A homogenizer from Silverson Machines Inc. for about 15-30 minutes. The weight percentages for the foregoing ingredients, calculated by comparing the weight of each respective ingredient relative to the total weight of the liquid composition, are provided in Table 3. Table 3 also provides the weight percentage of spinetoram impurities in the liquid composition based on the values determined by the assay procedure described above.

TABLE 3

Example C

| Ingredients | Wt. % |
|---|---|
| Spinetoram | 4.0 |
| Spinetoram impurities | 0.8 |
| Egg Albumen | 28.22 |
| Celvol ® 205 | 6.4 |
| Reax ® 88A | 0.48 |
| Geropon ® SDS | 0.1 |
| Water | 60.0 |

The liquid composition of Example C was later used for bio-efficacy experiments, but an assay was performed beforehand to determine its proportion by weight of pure spinetoram so appropriate concentrations for testing could be prepared. The assay was performed according to the procedure described above with respect to Example A and the weight percentage of the pure spinetoram component for the liquid composition was calculated to be 4.0%.

Example D

A portion of the liquid composition prepared in Example C was spray-dried using a Buchi® Model 190 bench top spray dryer from Buchi Corporation at about a 300-400 ml/hr feed rate, 4-6 bar nozzle pressure, 115-140° C. inlet temperature and 50-100° C. outlet temperature to provide Example D as a solid composition. It is believed that the spray drying process removes all or substantially all of the water and other volatile ingredients from the liquid composition of Example C as it is converted to the solid composition of Example D. Since none of the ingredients in the liquid composition of Example C apart from the water is believed to be volatile, the weight percentages for each of the ingredients in the solid composition of Example D were determined on the basis of all water being removed from the liquid composition of Example C during the spray drying. These weight percentages are set forth in Table 4.

TABLE 4

| Example D | |
|---|---|
| Ingredients | Wt. % |
| Spinetoram | 10.0 |
| Spinetoram impurities | 2.0 |
| Egg Albumen | 70.56 |
| Celvol ® 205 | 16.0 |
| Reax ® 88A | 1.2 |
| Geropon ® SDS | 0.24 |

The solid composition of Example D was later used for bio-efficacy experiments, but an assay was performed beforehand to determine its proportion by weight of pure spinetoram so appropriate concentrations for testing could be prepared. The assay was performed according to the procedure described above with respect to Example B and the weight percentage of the pure spinetoram component for the powder composition of Example D was calculated to be 9.6%.

Example E

A liquid composition including spinetoram, iron (III) oxide and a polyvinyl pyrolidone product, among other ingredients, was prepared according to the following. Spinetoram, Kraftsperse® 25M, a dispersant commercially available from MeadWestvaco Corporation, P.O. Box 118005, Charleston, S.C. 29423, Soprophor® 3D33, a surfactant commercially available from Rhodia, Inc., 8 Cedar Brook Drive, Cranbury, N.J. 08512, Dow Corning® 200, an anti-foaming agent commercially available from Dow Corning Corporation, P.O. Box 994, Midland, Mich. 48686, Proxel® GXL, a microbiostat solution commercially available from Arch Chemicals, Inc., 1955 Lake Park Drive, Suite 100, Smyrna, Ga. 30080, and a balance of water to provide a suspension concentrate having 25-50% w/w of spinetoram were mixed together. The resulting mixture was milled in an Eiger Mini Motormill media mill to a particle size of 1-10 μm (volume weighted mean diameter). The particle size was measured using a Malvern Mastersizer 2000 laser diffraction particle analyzer. After milling, 500M, an iron (III) oxide product commercially available from Magnetics International, Inc., Foster Plaza No. 7, 661 Andersen Drive, Pittsburgh, Pa. 15220, and a 5% w/w aqueous solution of Agrimer VA 6, a vinyl pyrolidone/vinylacetate co-polymer at a 4:6 ratio, (lot#5600168453) commercially available from International Specialty Products, Inc., 1361 Alps Road, Wayne, N.J. 07470, were added to the mixture under agitation. The 5% w/w aqueous solution of Agrimer VA 6 was prepared by mixing appropriate amounts of the Agrimer VA 6 with water. The total solids concentration of the mixture was adjusted in the range of 20-50% by weight by adding water. The mixture was then homogenized with a Silverson L4RT-A homogenizer for about 15-30 minutes. The weight percentages for the foregoing ingredients, calculated by comparing the weight of each respective ingredient relative to the total weight of the composition, are provided in Table 5. Table 5 also provides the weight percentage of spinetoram impurities in the composition based on the values determined by the assay procedure described above.

TABLE 5

| Example E | |
|---|---|
| Ingredients | Wt. % |
| Spinetoram | 7.18 |
| Spinetoram impurities | 1.17 |
| $Fe_2O_3$ | 12.15 |
| Agrimer VA 6 | 1.09 |
| Kraftsperse ® 25M | 1.17 |
| Soprophor ® 3D33 | 0.28 |
| Dow Corning ® 200 | 0.03 |
| Proxel ® GXL | 0.02 |
| Water | 76.91 |

The liquid composition of Example E was later used for bio-efficacy experiments, but an assay was performed beforehand to determine its proportion by weight of pure spinetoram so appropriate concentrations for testing could be prepared. The assay was performed according to the procedure described above with respect to Example A and the weight percentage of the pure spinetoram component for the liquid composition was calculated to be 6.2%.

Example F

A portion of the liquid composition prepared in Example E was spray-dried using a Buchi® Model 190 bench top spray dryer from Buchi Corporation at about a 300-400 ml/hr feed rate, 4-6 bar nozzle pressure, 115-140° C. inlet temperature and 50-100° C. outlet temperature to provide Example F as a solid composition. It is believed that the spray drying process removes all or substantially all of the water and other volatile ingredients from the liquid composition of Example E as it is converted to the solid composition of Example F. Since none of the ingredients in the liquid composition of Example E apart from the water is believed to be volatile, the weight percentages for each of the ingredients in the solid composition of Example F were determined on the basis of all water being removed from the liquid composition of Example E during the spray drying. These weight percentages are set forth in Table 6.

TABLE 6

| Example F | |
|---|---|
| Ingredients | Wt. % |
| Spinetoram | 31.1 |
| Spinetoram impurities | 5.08 |
| $Fe_2O_3$ | 52.63 |

TABLE 6-continued

Example F

| Ingredients | Wt. % |
|---|---|
| Agrimer VA 6 | 4.71 |
| Kraftsperse ® 25M | 5.06 |
| Soprophor ® 3D33 | 1.2 |
| Dow Corning ® 200 | 0.14 |
| Proxel ® GXL | 0.08 |

The solid composition of Example F was later used for bio-efficacy experiments, but an assay was performed beforehand to determine its proportion by weight of pure spinetoram so appropriate concentrations for testing could be prepared. The assay was performed according to the procedure described above with respect to Example B and the weight percentage of the pure spinetoram component for the powder composition of Example F was calculated to be 31.3%.

Example G

Another portion of the liquid composition prepared in Example E was spray-dried using a Buchi® Model 190 bench top spray dryer from Buchi Corporation at about a 300-400 ml/hr feed rate, 4-6 bar nozzle pressure, 150° C. inlet temperature and 50-100° C. outlet temperature to provide Example G as a solid composition. It is believed that the spray drying process removes all or substantially all of the water and other volatile ingredients from the liquid composition of Example E as it is converted to the solid composition of Example G. Since none of the ingredients in the liquid composition of Example E apart from the water is believed to be volatile, the weight percentages for each of the ingredients in the solid composition of Example G were determined on the basis of all water being removed from the liquid composition of Example E during the spray drying. These weight percentages are set forth in Table 7.

TABLE 7

Example G

| Ingredients | Wt. % |
|---|---|
| Spinetoram | 31.1 |
| Spinetoram impurities | 5.08 |
| $Fe_2O_3$ | 52.63 |
| Agrimer VA 6 | 4.71 |
| Kraftsperse ® 25M | 5.06 |
| Soprophor ® 3D33 | 1.2 |
| Dow Corning ® 200 | 0.14 |
| Proxel ® GXL | 0.08 |

The solid composition of Example G was later used for bio-efficacy experiments, but an assay was performed beforehand to determine its proportion by weight of pure spinetoram so appropriate concentrations for testing could be prepared. The assay was performed according to the procedure described above with respect to Example B and the weight percentage of the pure spinetoram component for the powder composition of Example G was calculated to be 34.57%.

Example H

Another portion of the liquid composition prepared in Example E was spray-dried using a Buchi® Model 190 bench top spray dryer from Buchi Corporation at about a 300-400 ml/hr feed rate, 4-6 bar nozzle pressure, 170° C. inlet temperature and 50-100° C. outlet temperature to provide Example H as a solid composition. It is believed that the spray drying process removes all or substantially all of the water and other volatile ingredients from the liquid composition of Example E as it is converted to the solid composition of Example H. Since none of the ingredients in the liquid composition of Example E apart from the water is believed to be volatile, the weight percentages for each of the ingredients in the solid composition of Example H were determined on the basis of all water being removed from the liquid composition of Example E during the spray drying. These weight percentages are set forth in Table 8.

TABLE 8

Example H

| Ingredients | Wt. % |
|---|---|
| Spinetoram | 31.1 |
| Spinetoram impurities | 5.08 |
| $Fe_2O_3$ | 52.63 |
| Agrimer VA 6 | 4.71 |
| Kraftsperse ® 25M | 5.06 |
| Soprophor ® 3D33 | 1.2 |
| Dow Corning ® 200 | 0.14 |
| Proxel ® GXL | 0.08 |

The solid composition of Example H was later used for bio-efficacy experiments, but an assay was performed beforehand to determine its proportion by weight of pure spinetoram so appropriate concentrations for testing could be prepared. The assay was performed according to the procedure described above with respect to Example B and the weight percentage of the pure spinetoram component for the powder composition of Example H was calculated to be 35.33%.

As indicated above, the solid composition provided after spray drying will include a ratio by weight between the pesticide and the at least one co-ingredient that is the same as or substantially equivalent to the ratio by weight between the pesticide and the at least one co-ingredient in the liquid composition. For example, with respect to Examples A and B, Example A includes a 3.2:1 ratio by weight between zinc oxide and spinetoram, a 5.1:1 ratio by weight between egg albumen and spinetoram and a 1.6:1 ratio by weight between egg albumen and zinc oxide, while Example B includes a 3.3:1 ratio by weight between zinc oxide and spinetoram, a 5.1:1 ratio by weight between egg albumen and spinetoram and a 1.6:1 ratio by weight between egg albumen and zinc oxide. With respect to Examples C and D, Example C includes a 7.1:1 ratio by weight between egg albumen and spinetoram, a 1.6:1 ratio by weight between polyvinyl alcohol and spinetoram and a 4.4:1 ratio by weight between egg albumen and polyvinyl alcohol, while Example D includes a 7.1:1 ratio by weight between egg albumen and spinetoram, a 1.6:1 ratio by weight between polyvinyl alcohol and spinetoram and a 4.4:1 ratio by weight between egg albumen and polyvinyl alcohol. With respect to Examples E and F, G, and H, Example E includes a 1.7:1 ratio by weight between iron (III) oxide and spinetoram, a 0.2:1 ratio by weight between Agrimer VA 6 and spinetoram and a 0.1:1 ratio by weight Agrimer VA 6 and iron (III) oxide, while Examples F, G and H each include a 1.7:1 ratio by weight between iron (III) oxide and spinetoram, a 0.2:1 ratio by weight between Agrimer VA 6 and spinetoram and a 0.1:1 ratio by weight between Agrimer VA 6 and iron (III) oxide. Each of the weight ratios set forth above in this paragraph was rounded to the nearest tenth.

Bio-Efficacy Testing

Biological efficacy experiments were conducted according to the following parameters. A spinetoram control solution was prepared utilizing either Radiant®, a suspension concentrate formulation of spinetoram, or Delegate®, a water-dispersible granule formulation of spinetoram, in water to obtain a spinetoram concentration in solution of 125 ppm. Radiant® and Delegate® are commercially available from Dow AgroSciences LLC, 9330 Zionsville Road, Indianapolis, Ind., 46268. Test solutions were also prepared utilizing the liquid compositions of Examples A, C and E and the solid compositions of Examples B, D and F-H (collectively the Example A-H solutions) in water to obtain a spinetoram concentration in each solution of 125 ppm. These solutions, plus a water-only control, were applied to potted pepper plants (*Capsicum annuum*) using a Mandel track sprayer calibrated to deliver the equivalent of 200 L/Ha of spray. Treated plants were allowed to dry and then were aged outdoors in natural sunlight or under a set of lamps emitting ultraviolet light at levels comparable to natural sunlight. At the appropriate time after treatment, i.e., at 4, 7 and 10; 4, 7 and 11; or 5 and 10 days after treatment, 2.5 cm diameter disks were cut from treated leaves. One leaf disk was placed in each well of a 32 well plastic tray, which also contained a thin layer of agar to provide moisture. There were 8 replicate disks per treatment. Each well was infested with three second instar beet armyworm (*Spodoptera exigua*) larvae, and the well was sealed with plastic film. Larvae were held in an environmental chamber at 25° C./40 percent relative humidity. At 48 hours after infestation, the larvae were graded for mortality. A larva was considered dead if it could not move after being prodded, and the percent mortality (percent control) was calculated.

For Examples I-IV, Table 9 below provides the percent control of the insect associated with the spinetoram control solution relative to an untreated standard. For the Example A-H solutions, Table 9 provides the improvement in percent control relative to the spinetoram control solution (i.e., (percent control by Example A-H solutions)-(percent control by spinetoram control solution)). Table 9 also provides the average improvement over the spinetoram control solution which was calculated by summing the individual improvements for each of the days relative to the control and then dividing by the number of measurements. As illustrated in Table 9, the Example B, D and F-H solutions, which utilized the solid compositions provided by the spray drying, exhibited enhanced pesticidal activity relative to the Example A, C and E solutions, respectively.

TABLE 9

| Example Composition | 3 DAT | 4 DAT | 5 DAT | 6 DAT | 7 DAT | 9 DAT | 10 DAT | 11 DAT | 12 DAT | 13 DAT | 14 DAT | Average Improvement |
|---|---|---|---|---|---|---|---|---|---|---|---|---|
| Example I | | | | | | | | | | | | |
| Spinetoram Control Solution | — | 88 | — | — | 25 | — | 8 | — | — | — | — | |
| Example A Solution | — | 8 | — | — | 33 | — | 17 | — | — | — | — | 19 |
| Example B Solution | — | 4 | — | — | 58 | — | 58 | — | — | — | — | 40 |
| Example II | | | | | | | | | | | | |
| Spinetoram Control Solution | — | 67 | — | — | 33 | — | — | 25 | — | — | — | |
| Example C Solution | — | 21 | — | — | 29 | — | — | −21 | — | — | — | 10 |
| Example D Solution | — | 33 | — | — | 58 | — | — | 29 | — | — | — | 40 |
| Example III | | | | | | | | | | | | |
| Spinetoram Control Solution | | | 58 | | | | 17 | | | | | |
| Example E Solution | | | 21 | | | | 21 | | | | | 21 |
| Example G Solution | | | 25 | | | | 41 | | | | | 33 |
| Example H Solution | | | 25 | | | | 50 | | | | | 38 |
| Example IV | | | | | | | | | | | | |
| Spinetoram Control Solution | | | 75 | | | | 8 | | | | | |
| Example F Solution | | | 25 | | | | 88 | | | | | 57 |

The headings in this document are for convenience only and must not be used to interpret any portion thereof.

Any theory, mechanism of operation, proof, or finding stated herein is meant to further enhance understanding of the present invention and is not intended to make the present invention in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one,"

"at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the invention has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A method, comprising:
providing a liquid composition that includes spinetoram, ferric oxide and a polymeric material that includes polyvinyl pyrrolidone; and
spray drying the liquid composition to provide a solid composition wherein the solid composition exhibits enhanced pesticidal activity compared to the liquid composition.

2. The method of claim 1, wherein the spray drying includes reducing water from at least about 20% by weight in the liquid composition to less than about 10% by weight in the solid composition.

3. The method of claim 1, wherein the spray drying includes reducing water from at least about 50% by weight in the liquid composition to less than about 5% by weight in the solid composition.

4. A composition, comprising a spray dried material including at least one spinosyn and at least two co-ingredients that enhance pesticidal activity of the composition compared to a composition dissimilar only in not having the at least two co-ingredients, wherein the spray dried material exhibits enhanced pesticidal activity compared to a liquid composition that includes the at least one spinosyn and the at least two co-ingredients in a ratio by weight that is substantially equivalent to a ratio by weight between the at least one spinosyn and the at least two co-ingredients in the spray dried material, and wherein the at least two co-ingredients comprise at least one metal oxide and at least one polymeric material.

5. The composition of claim 4, wherein the spray dried material includes less than about 10% by weight of water.

6. The composition of claim 4, wherein the spray dried material includes less than about 4% by weight of water.

7. The composition of claim 4, wherein the spray dried material includes from about 0.001% to about 2% by weight of water.

8. The composition of claim 4, wherein the at least one spinosyn comprises spinetoram, the at least one metal oxide comprises ferric oxide, and the at least one polymeric material includes polyvinyl pyrrolidone.

9. A method of controlling insects which comprises applying to a locus where control is desired an insect-inactivating amount of a composition according to claim 4.

* * * * *